US007653509B2

(12) United States Patent
Bagwell

(10) Patent No.: US 7,653,509 B2
(45) Date of Patent: Jan. 26, 2010

(54) PROBABILITY STATE MODELS

(75) Inventor: C. Bruce Bagwell, Topsham, ME (US)

(73) Assignee: Verity Software House, Topsham, ME (US)

( * ) Notice: Subject to any disclaimer, the term of this patent is extended or adjusted under 35 U.S.C. 154(b) by 36 days.

(21) Appl. No.: 11/897,148

(22) Filed: Aug. 29, 2007

(65) Prior Publication Data

US 2009/0063095 A1 Mar. 5, 2009

(51) Int. Cl.
*G06F 17/18* (2006.01)
(52) U.S. Cl. .............................. 702/181; 702/19; 702/21
(58) Field of Classification Search .................. 702/19, 702/21, 179, 181, 194; 707/100, 104.1; 422/82.05; 435/7.24
See application file for complete search history.

(56) References Cited

U.S. PATENT DOCUMENTS 5,224,058 A 6/1993 Mickaels et al.
5,605,805 A 2/1997 Verwer et al.
6,178,382 B1 1/2001 Roederer et al.
6,366,870 B2* 4/2002 Jarman et al. ............... 702/179
6,592,822 B1 7/2003 Chandler
6,954,722 B2 10/2005 Parks et al.
7,043,500 B2 5/2006 Leary
7,299,135 B2 11/2007 Thayer
2003/0009470 A1 1/2003 Leary
2006/0080040 A1* 4/2006 Garczarek et al. ............. 702/19
2007/0118297 A1 5/2007 Thayer

* cited by examiner

*Primary Examiner*—John H Le
(74) *Attorney, Agent, or Firm*—Pierce Atwood LLP; Kevin M. Farrell; Katherine A. Wrobel

(57) ABSTRACT

The present invention provides a method of analyzing multi-dimensional data using a computer as well as methods of displaying multidimensional data to a user for further analysis. The present invention provides for a method and system for state model Fitting. The system components include a detector and a computer operably connected to the detector. The computer accesses one or more logic instructions for receiving and analyzing raw data from the detector and generating a state model of the raw data based on probability weights.

21 Claims, 16 Drawing Sheets

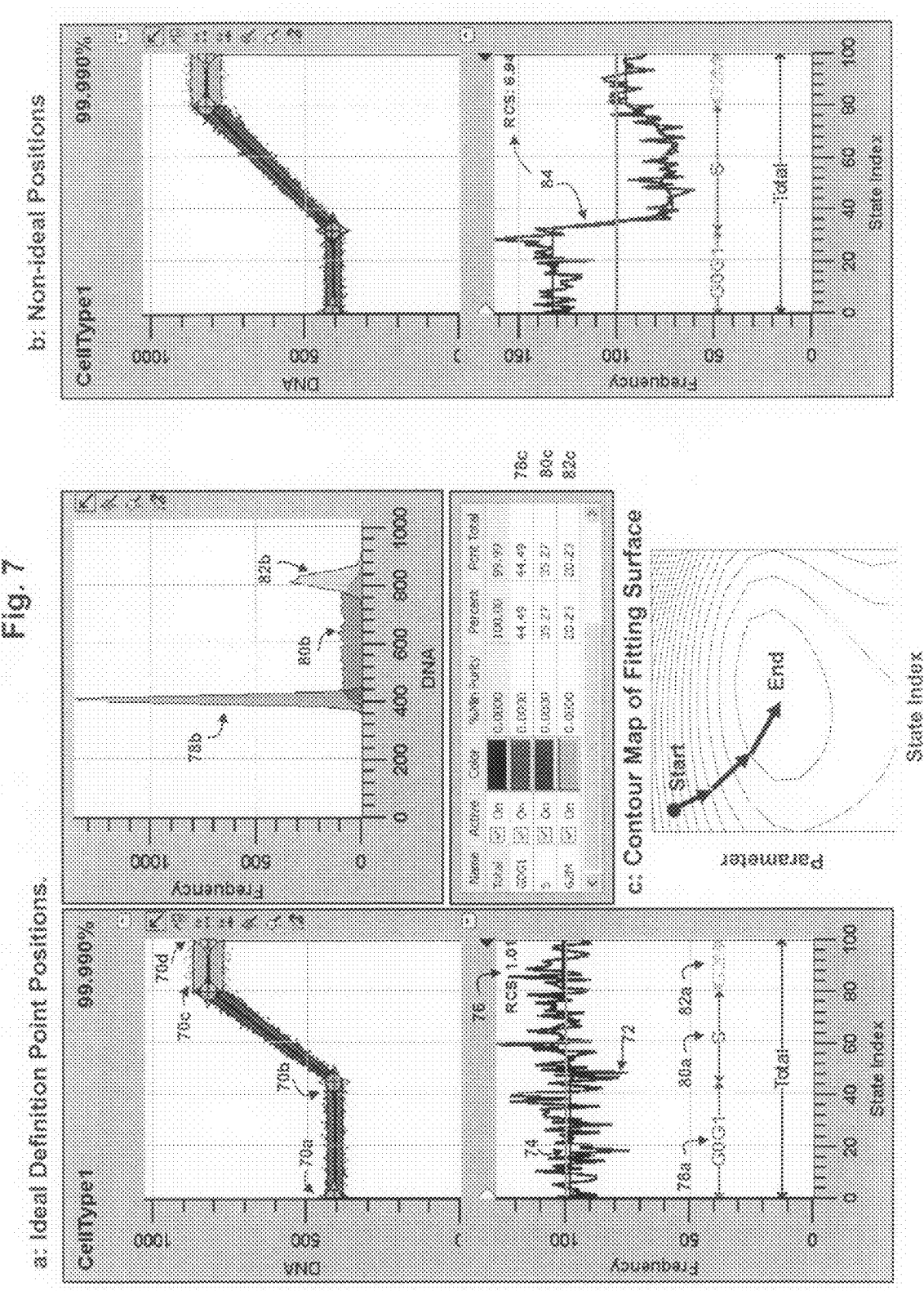

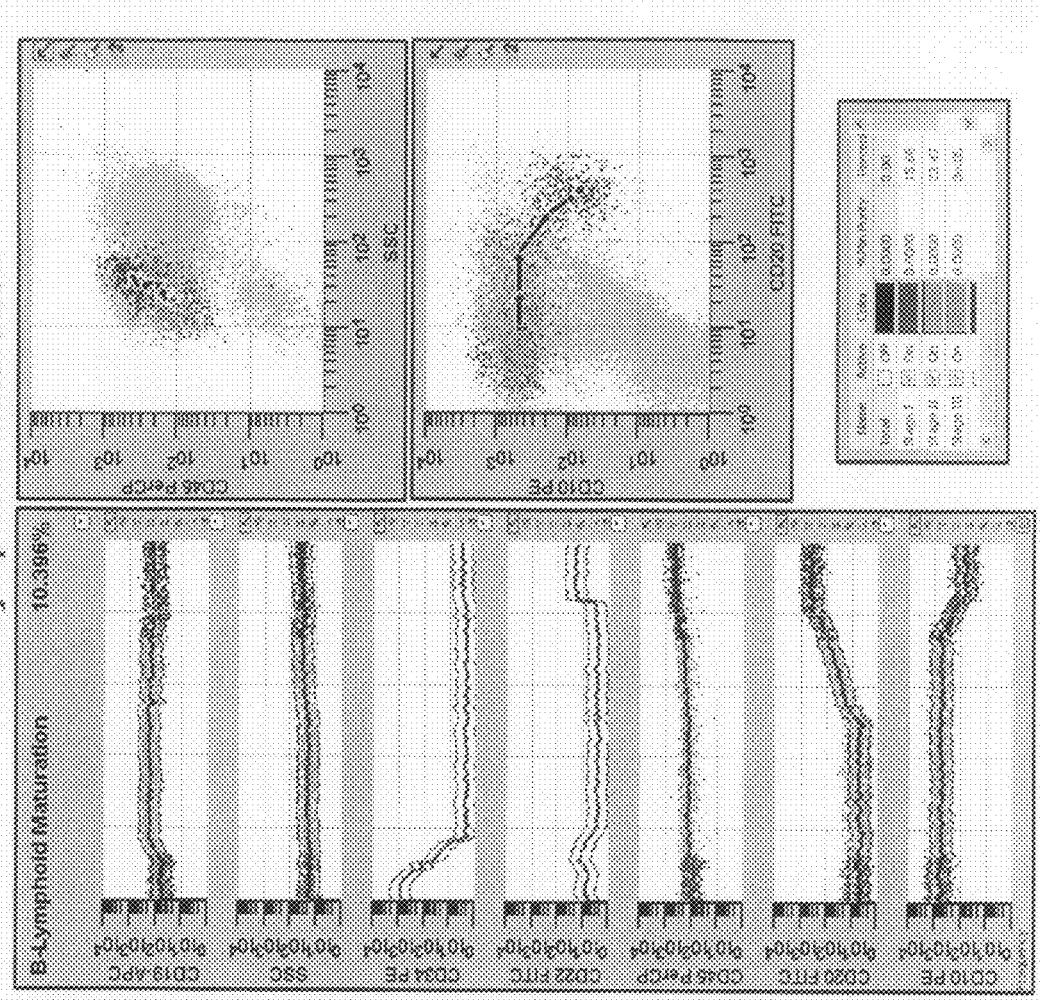
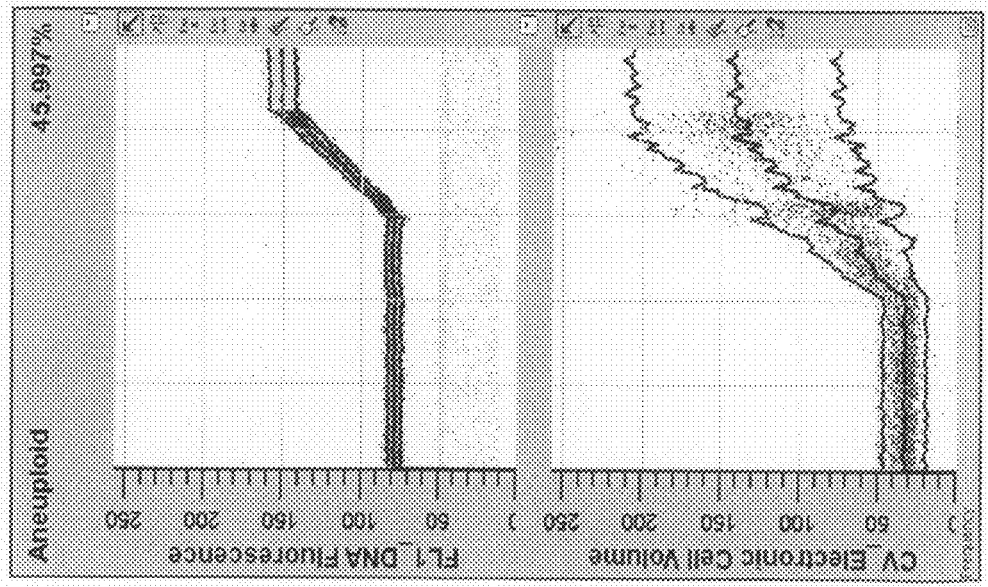
Fig. 14

PROBABILITY STATE MODELS

FIELD OF THE INVENTION

The present invention relates to a computer program and methods of analyzing multidimensional data using a computer. The computer program and methods of the present invention analyze multidimensional data that can be represented by one or more state models.

BACKGROUND OF THE INVENTION

Presently there are a number of methods for analyzing multidimensional data. Typically, these methods rely on some form of mathematical modeling which is used to present, rearrange or transform the data in such a way that observations may be made and conclusions drawn. Such methods include for example, multivariate analysis, regression analysis, and logarithmic transformation. Although there are a number of methods to analyze multidimensional data, the methods have certain limitations and shortcomings. For example, when using visualization to analyze such data, the viewing of multidimensional data as combinations of lower dimensional views (e.g., histograms and bivariate displays) results in the loss of information in an uncontrollable manner. Such loss of information frequently leads to loss of the pertinent information necessary to accomplish desired goals, e.g., understanding the differentiation and maturation of cells when analyzing cytometry data. While such methods generally are not dependent upon the manner of data collection, in many instances those who collect data by a particular method routinely use the same form(s) of data analysis and presentation. This is especially true in the field of cytometry.

Cytometry is a technique for the simultaneous analysis of multiple physical and chemical characteristics of individual particles either suspended in a liquid medium (flow cytometry) or coated on slides (image cytometry). Typically cytometry is used for the analysis of the physical and chemical characteristics of individual cells, although any type of particle can be measured by this technology. The term "cell" will refer to a particle that is measured by a cytometer. Cytometry uses the principles of light scattering, light excitation, cell volume, and emission of fluorochrome molecules to generate specific multi-parameter data from a single cell. The process of collecting correlated data from a population of cells using a cytometer is summarized in FIG. 1. The cells are normally collected as a tissue specimen and then divided into one or more samples. The samples can be contained either in a fluid volume (FIG. 1a, 12a) or on a slide (FIG. 1b, 12b).

The sample is normally reacted with reporter molecules or stains that confer information about the quantity of specific types of cellular structures or molecules either on or in the cell. The cocktail of stains along with the cell's intrinsic properties allow different cell types to be partially or completely delineated from each other in subsequent analyses. Stains can include one or more fluorescent labeled monoclonal antibodies, nucleic acid specific fluorescent components, fluorescent lipophilic molecules, viable cell dyes, etc. The intrinsic properties of the cells include, but are not limited to, forward angle light scattering (FALS), side scatter (SS) and cell volume.

In FIG. 1, the differently filled circles 10a, 10b, 10c represent three different cell types that are present for this example population. Cell types are known types of cells that are defined by a priori information from previous studies and/or the data collected by the cytometer. These cell types include, but are not limited to, tissue culture cell-lines, specific lineage-specific blood or bone-marrow cells, bacteria and fungi.

After staining, the cells are processed by a cytometer as illustrated in FIG. 1c. Depending on the staining cocktail, the intrinsic cellular properties, and the instrument's capability; various parameters are detected, digitized, and stored. This stored data structure is referred to as a listmode file. Typically, listmode files organize stored data such that measured parameters are in columns and events are in rows. Commonly, the number of events generated during cytometry analysis is in the range from about 10 to about 20,000. However, in certain instances the number of events can be in the millions.

The listmode correlated parameters are normally displayed as one-parameter (1P), two-parameter (2P), or three-parameter (3P) plots. (See FIG. 2.) Using techniques such as principal components, a higher number of correlated parameters (3+P) can also be displayed.

Analysis of multidimensional data, such as cytometer data generally involves classifying the data into relevant populations by using some set of hierarchical or refinement gates. A gate is either a one-dimensional range or a two-dimensional parameter boundary where events can either be inside or outside the boundary. Gates can also be combined into Boolean algebraic expressions. Events that satisfy these gates can then be displayed in other histograms defined by other parameters. This gate refinement process is carried out until the populations of interest are displayed on some set of histograms. Statistical analyses of these gated events along with all or some of the graphics are generally the ultimate output of conventional multidimensional data analysis, including cytometry analysis.

This prior art approach to analysis of multidimensional data, however, has several limitations, including parameter scalability, gating errors, and multiple sample data integration and visualization. The number of two-parameter histograms necessary to represent m-dimensional data encoded in a listmode file is $m*(m-1)/2$. For example, examining a sample with a cytometer that generates ten parameters requires 45 separate two-parameter histograms and a visual understanding of the implicit relationships between the parameters is very difficult. Thus, prior art approaches do not scale well with number of parameters.

The prior art method of analyzing multidimensional data is also limited by compounding gating errors. A gate is a boundary that attempts to contain one or more cellular populations, however, populations are actually m-dimensional probability distributions. Attempting to separate these distributions with simple boundaries can result in false positives contained in the gate and false negatives excluded by the gate. Since the output of one gate is used for the definition of another, these errors are compounded as the number of parameters increase. Compounding gating errors are further exacerbated by subjective placement of the gates.

The prior art method of analyzing multidimensional data is further limited in its ability to analyze data from multiple samples from a single specimen. Different cocktails of stains are often used to look at a single specimen in different ways. It is difficult to correlate the information from the separate analyses so that a single coherent picture of the specimen emerges.

Accordingly, there is a need in the art for improved methods of analyzing multidimensional data and related systems for analyzing and/or displaying data, including multidimensional data generated during cytometry analysis.

SUMMARY OF THE INVENTION

The present invention, which provides for methods of analyzing multidimensional data, overcomes many of the limitations of prior art analysis methods. In general, the present invention defines an additional parameter based on states and probabilities. This additional parameter, referred to as a state index, is then used to parametrically define all the other parameters in the data set. The boundaries defined by the state index are determined probabilistically where each state has equal probability of representation in the sample. Once the data is represented in this form, simple stacked graphics can display all parameter correlations. In other aspects the present invention provides a stochastic state index and cell type selection process that allows the system to account for population overlap and thus eliminate the need for gating.

Since state models are applicable to many cellular systems which include cell division, signal transduction cascade, lineage maturation, and differentiation; the present invention has particular relevance to the analysis of biochemical data and in particular analysis of data generated using a cytometer. In certain aspects, the present invention relates to the analysis of multidimensional data, including without limitation, continuous or discrete valued data. In a preferred embodiment, the present invention provides for the analysis of multidimensional data generated by a cytometer and more preferably, a flow cytometer. In other aspects, the present invention provides for the display of data that is easily understood by the user and further identifies portions of the analyzed data that are of interest to the user. In still other aspects, the present invention provides for data analysis systems, including without limitation, cytometry analysis systems and computer program products capable of carrying out the analysis methods of the present invention.

BRIEF DESCRIPTION OF THE DRAWINGS

FIG. 7 depicts one embodiment of the probability state model fitting process.

FIG. 14 depicts one embodiment of the multiparameter display output of the present invention.

DETAILED DESCRIPTION OF THE INVENTION

The invention and various specific aspects and embodiments thereof will be better understood with reference to the following drawings, appendix, and detailed descriptions and examples. In some of the drawings and detailed descriptions below, the present invention is described in terms of various embodiments involving the analysis and display of cytometry data, as well as systems for performing the same. However, this should not be taken to limit the invention, which, using the teachings provided herein, can be applied to the analysis and display of data generated by a variety of devices and systems, including without limitation, flow cytometric data, microarray data, cell sorting data, and imaging data.

Although the present invention is not limited to the analysis and/or display of any particular type of multidimensional data or data generated by any particular device or system, the present invention is particularly useful for data analysis of cytometric data and particularly data generated by a flow cytometer. As such, the present invention shall be described further herein with particular detail with respect to analysis of cell data as may be provided by a flow cytometry system.

Figure 3:
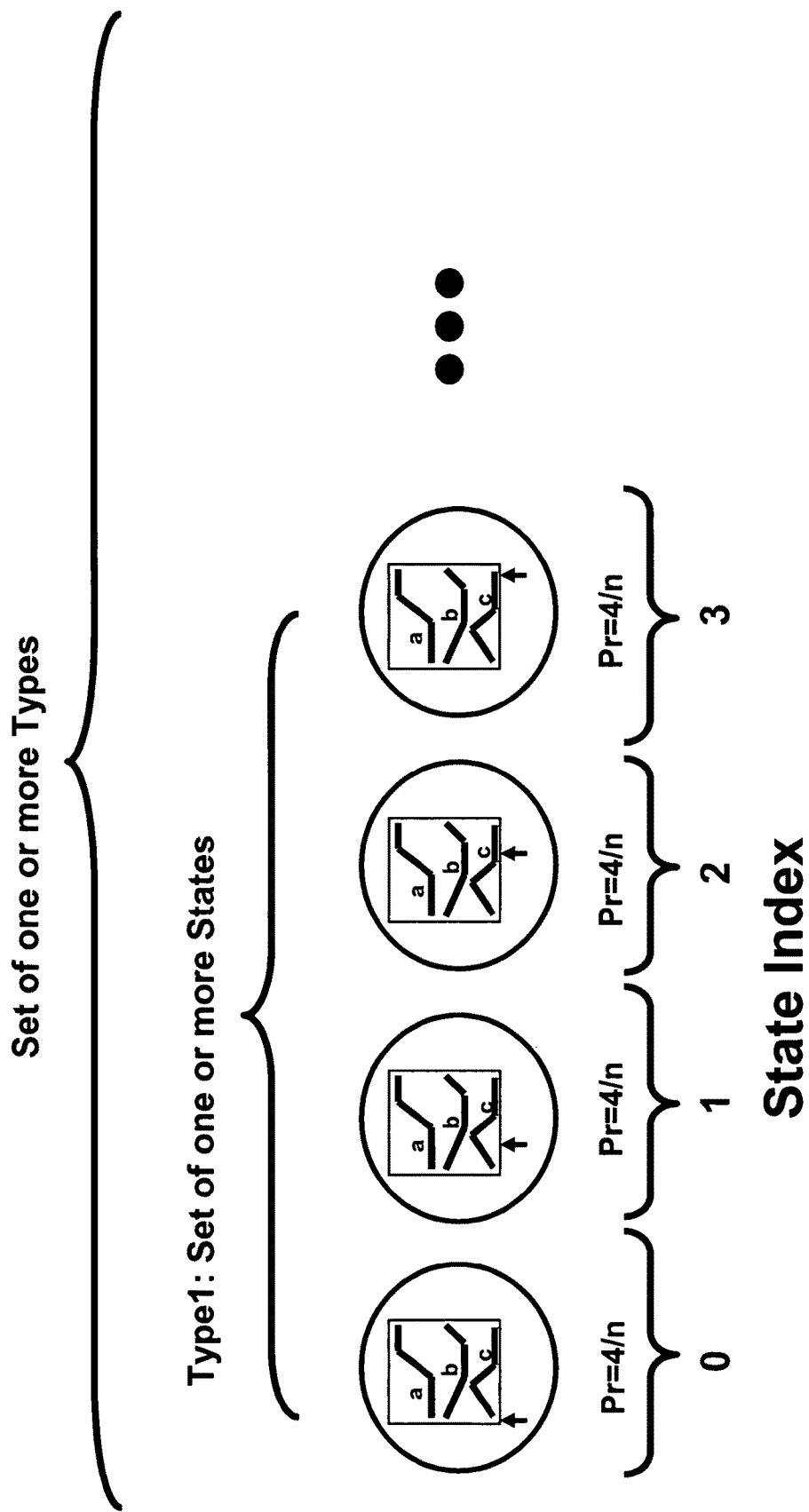
FIG. 3 illustrates a probability state model.

As used herein, the following terms are defined as follows:

The term "probability state model" refers to one or more types defined by a set of one or more states. Each state is composed of one or more parameter profiles. The boundaries that define a state require that each state have equal probability of occurrence. If there are n events in a type and r states, the probability of occurrence is given by r/n. One example of a probability state model is depicted in FIG. 3, where there are four states identified with State Index values of 0, 1, 2, and 3. Each state is composed of three parameter profiles (a, b, and c).

The term "cells" refers to entities that are measured by a detection device, which may include a photodiode, CCD camera, or other optical detection device that detects an optical or electronic signal.

The term "cell type" is a state model "type" defined by a data structure that is a collection of parameter profiles that define a specific population of cells and a set of states.

The term "cell type bias" refers to a normalization factor that allows different cell types with different state index resolutions and number of parameter profiles to be analyzed using the methods of the present invention.

The term "cytometry" refers to a set of technologies associated with measuring correlated parameters from cells.

The term "definition point" refers to a point in a parameter profile that has a specific parameter value and state index value.

The term "control definition point" is an entity that can move either by user intervention or by a modeling process that defines the intervening definition point's position. In certain embodiments control definition points can have restricted movement or alternatively may be related to one another by one or more mathematical relations.

The term "event" refers to a data value having one or more correlated parameters. In one embodiment an event is a digitized entity measured by a cytometer.

The term "listmode file" refers to a data structure that preserves the correlation between at least two data values.

One example of a listmode file is an electronic data file comprising at least one event and its correlated parameters. In a preferred embodiment, a listmode file is the output of a cytometer.

The term "parameter" refers to an attribute of a cell. In one embodiment, a parameter is an attribute of a cell that is measured by a cytometer.

The term "parameter profile" refers to a collection of definition points, control definition points, and relations between control definition points.

The term "state index" refers to a specific state in a probability state model. In one example the state index ranges from 0 to some arbitrary resolution such as 100.

The term "zone" refers to a state index range where the end points can be linked to specific control definition points.

Analysis of a Single Cell Type

Figure 1:
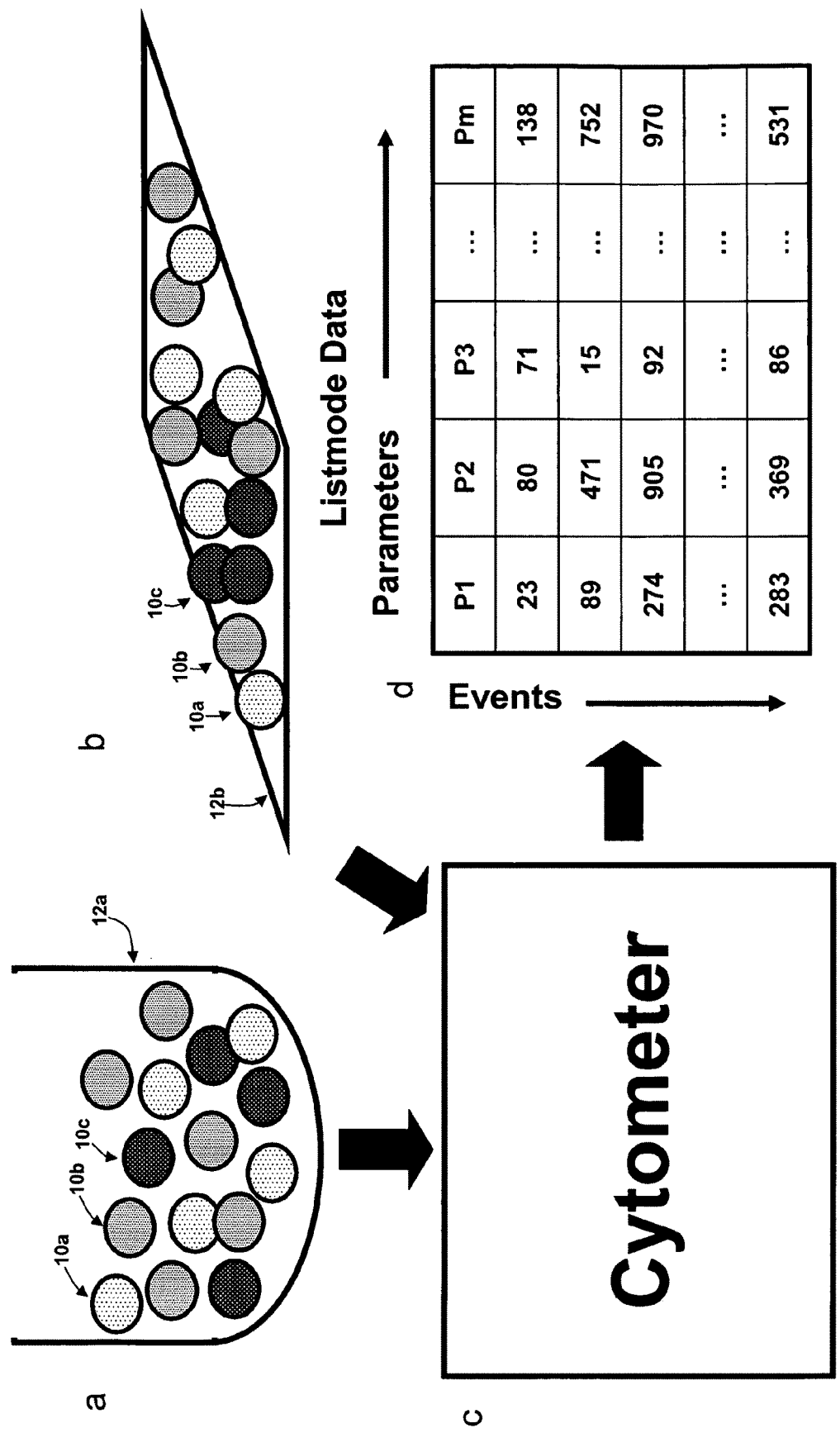
FIG. 1 illustrates a prior art method of generating a listmode file using a cytometer
Figure 2:
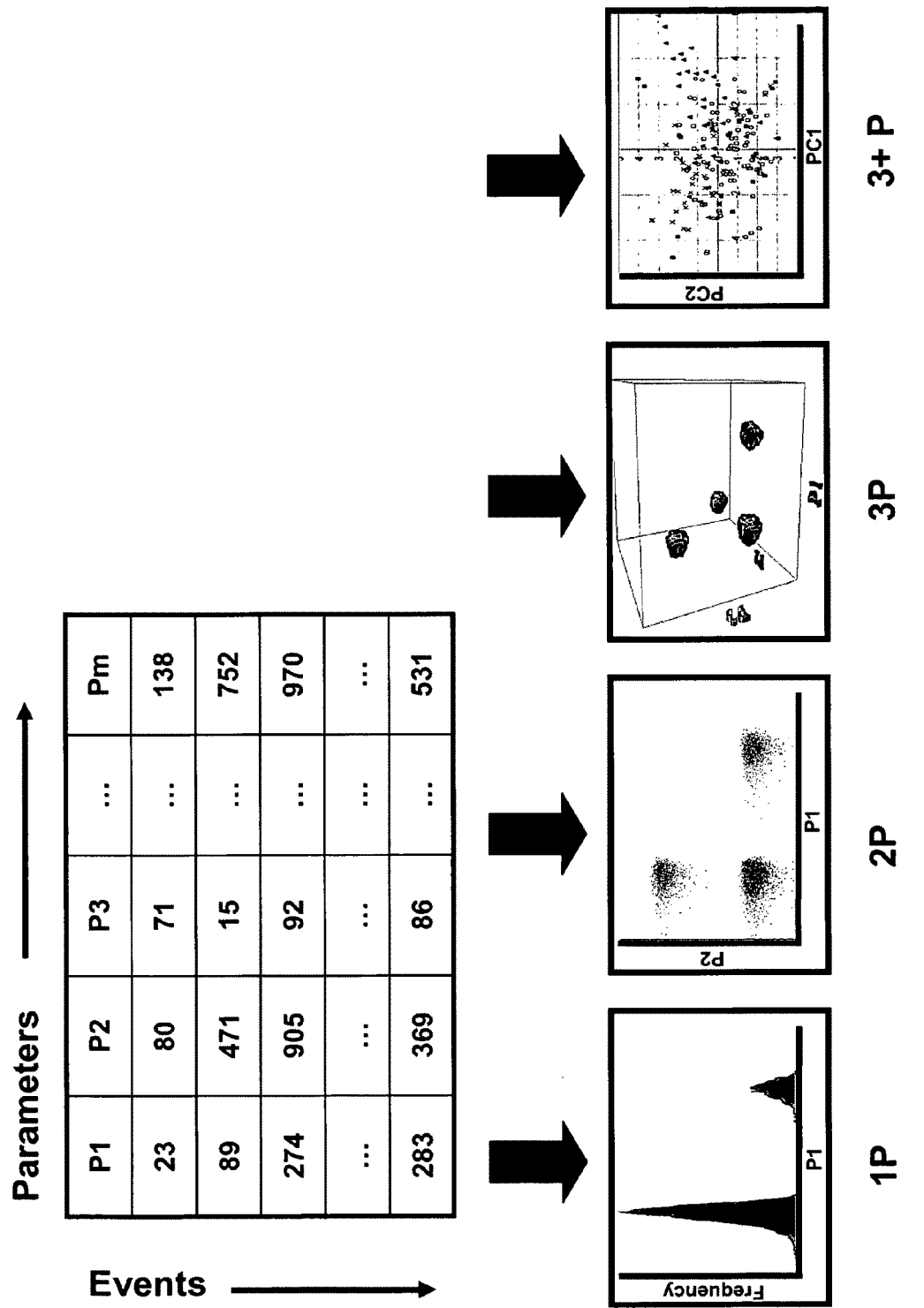
FIG. 2 illustrates prior art methods of displaying cytometry data.

According to the present invention analysis of a single cell type begins by receiving raw data at a computer. In certain embodiments, the raw data may already be in existence, for example the data may have been generated by an earlier analysis, or may be received directly from a device in communication with the computer carrying out the analysis. In a preferred embodiment, raw data is received by the computer as a listmode file generated by a cytometer and more preferably, a flow cytometer. Flow cytometers allow the user to obtain multidimensional data with respect to cells to be analyzed and are commercially available from number of sources, including Beckman Coulter, Inc. Fullerton, Calif. and BD Biosciences, San Jose, Calif. Illustrative examples of listmode files comprising a parameter value and corresponding event for each individual cell measured by the cytometer are shown in FIGS. 1 and 2.

Figure 4:
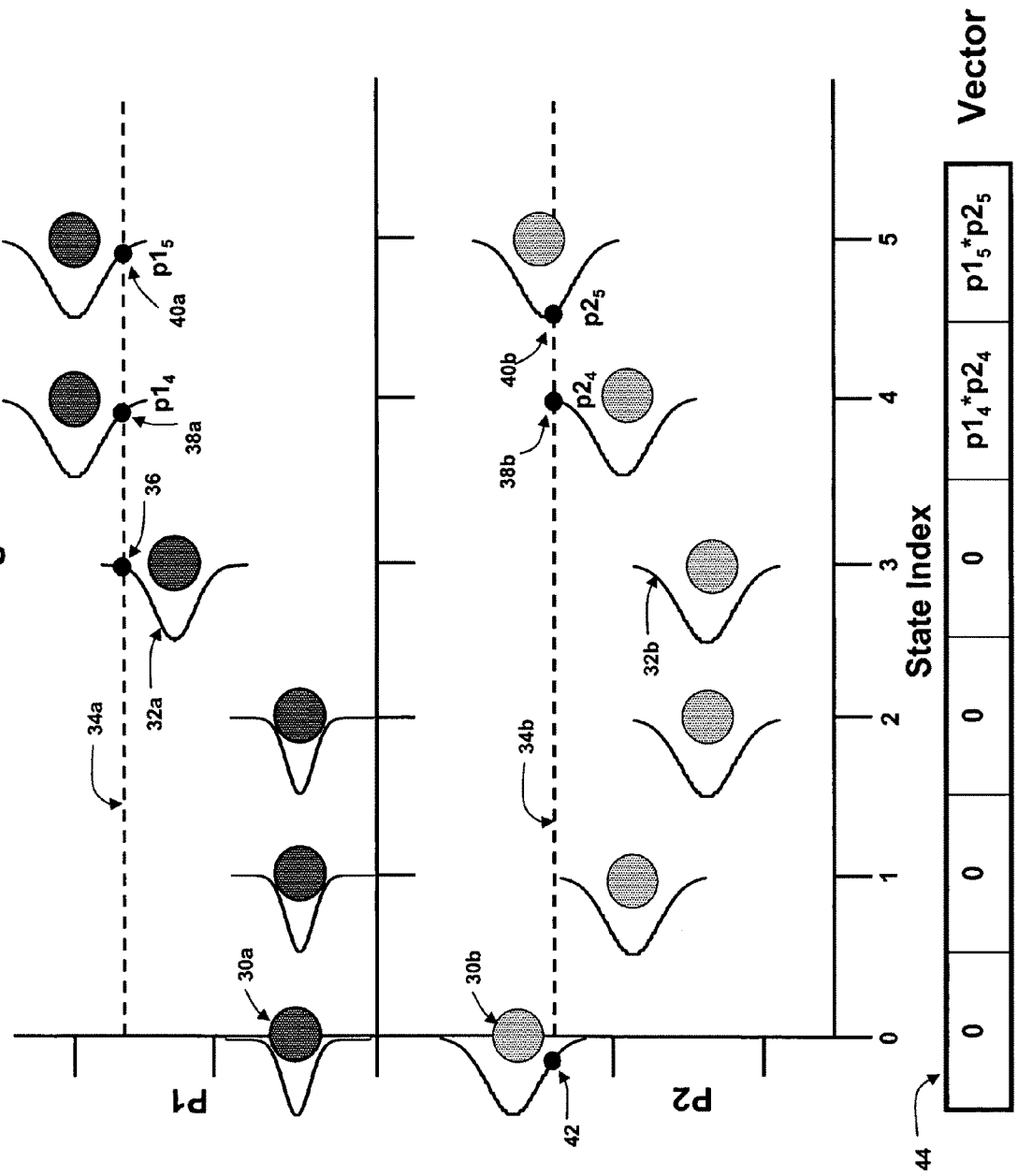
FIG. 4 depicts one embodiment for creating a selection vector for an event.

FIG. 4 illustrates one embodiment of the present invention for selecting a state index for a given set of parameters. As illustrated in FIG. 4, two parameters, P1 and P2, are distributed against a state index. In the present illustration it is assumed that the positions of all the definition points 30a, 30b are appropriate for the input data and that the measurement probability distributions 32a, 32b for each definition point are known. In other embodiments of the present invention, the position of the definition points and their corresponding probability distributions are unknown and are determined as set forth below in the description of FIGS. 6, 7A, 7B and 7C.

FIG. 4 further illustrates that for each parameter value there is a corresponding event 34a, 34b, which may be depicted as dashed lines. In certain instances the event values intersect their respective definition point probability distributions 36, 38a, 38b, 40a, 40b, 42 at locations that have probabilities. In one embodiment, the paired significant probabilities for each state index 38a and 38b, 40a and 40b are converted to probability weights by multiplication. In other embodiments the selection vector values may be calculated using other methods, including but not limited to, Chi-square and methods accounting for parameter correlation A selection vector 44 contains all the probability weights for all the state indices for one event defined in the model for a particular cell type.

Figure 5:
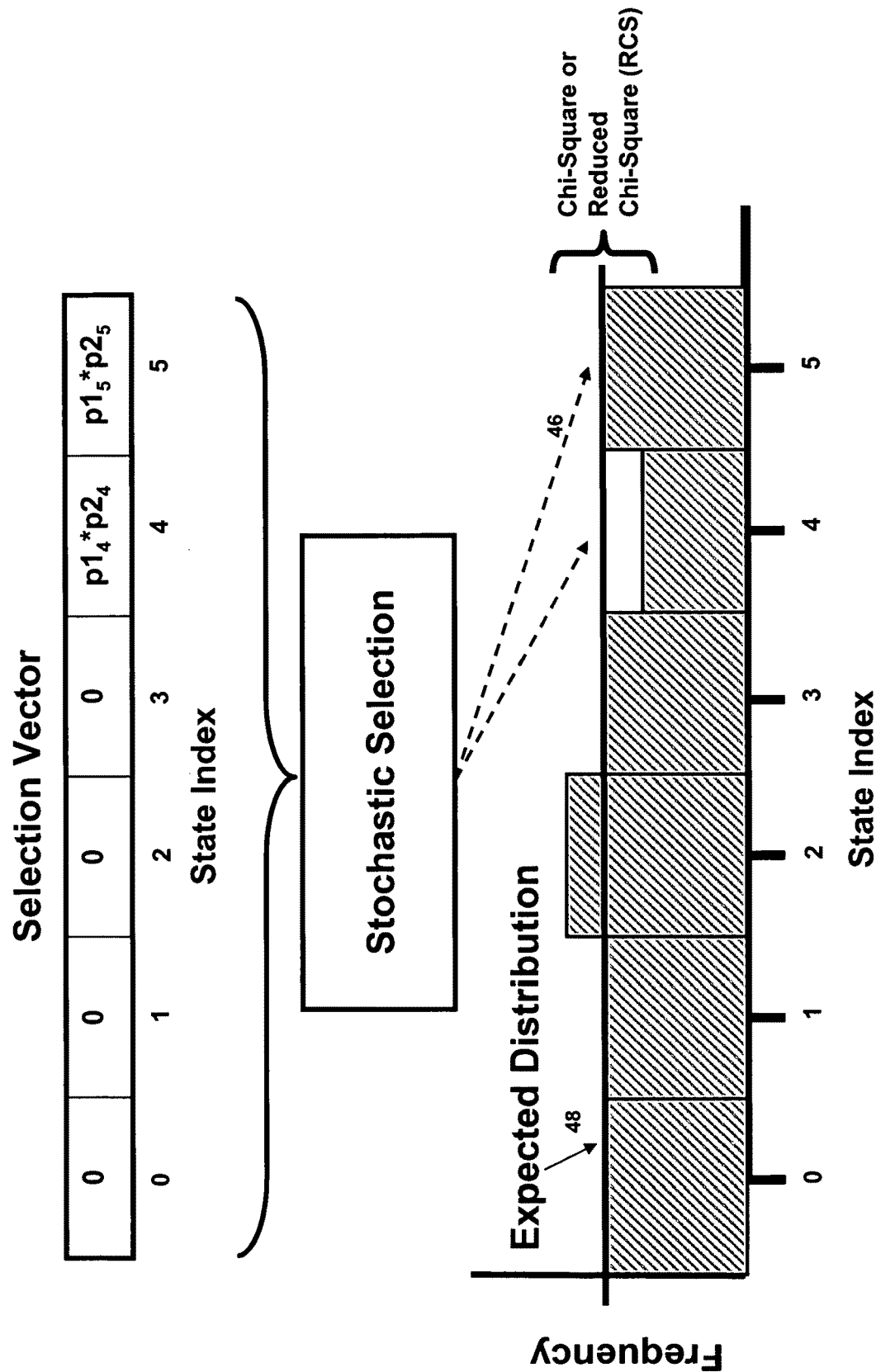
FIG. 5 depicts the process of selecting a state index from the selection vector.

In the embodiment illustrated in FIG. 4, all probability weights are approximately zero except for state indices 4 and 5. This collection of probability weights can then be used to stochastically select a specific state index as illustrated in FIG. 5. In one embodiment the stochastic selection is carried out using an algorithm which results in the selection of a specific state index that is probability weighted.

Turning to FIG. 5, once a state index is chosen, a corresponding state index counter 46 is incremented. This process ultimately forms a state index frequency distribution 48 after all the events have been processed. In a preferred embodiment the expected frequency distribution 48 is uniform for ideally placed definition points and represents the average frequency from all state indices. In other embodiments the expected frequency distribution 48 may include, but is not limited to, other distributions such as the exponential. A smoother form of the frequency distribution 48 can be obtained by summing the probability weights directly. The degree of deviation between the observed frequency distribution and the expected distribution 48 can be quantified by a number of statistics, including without limitation Chi-square and Reduced Chi-square (RCS) statistics. This deviation from uniformity is referred to as the "uniformity response value".

Figure 6:
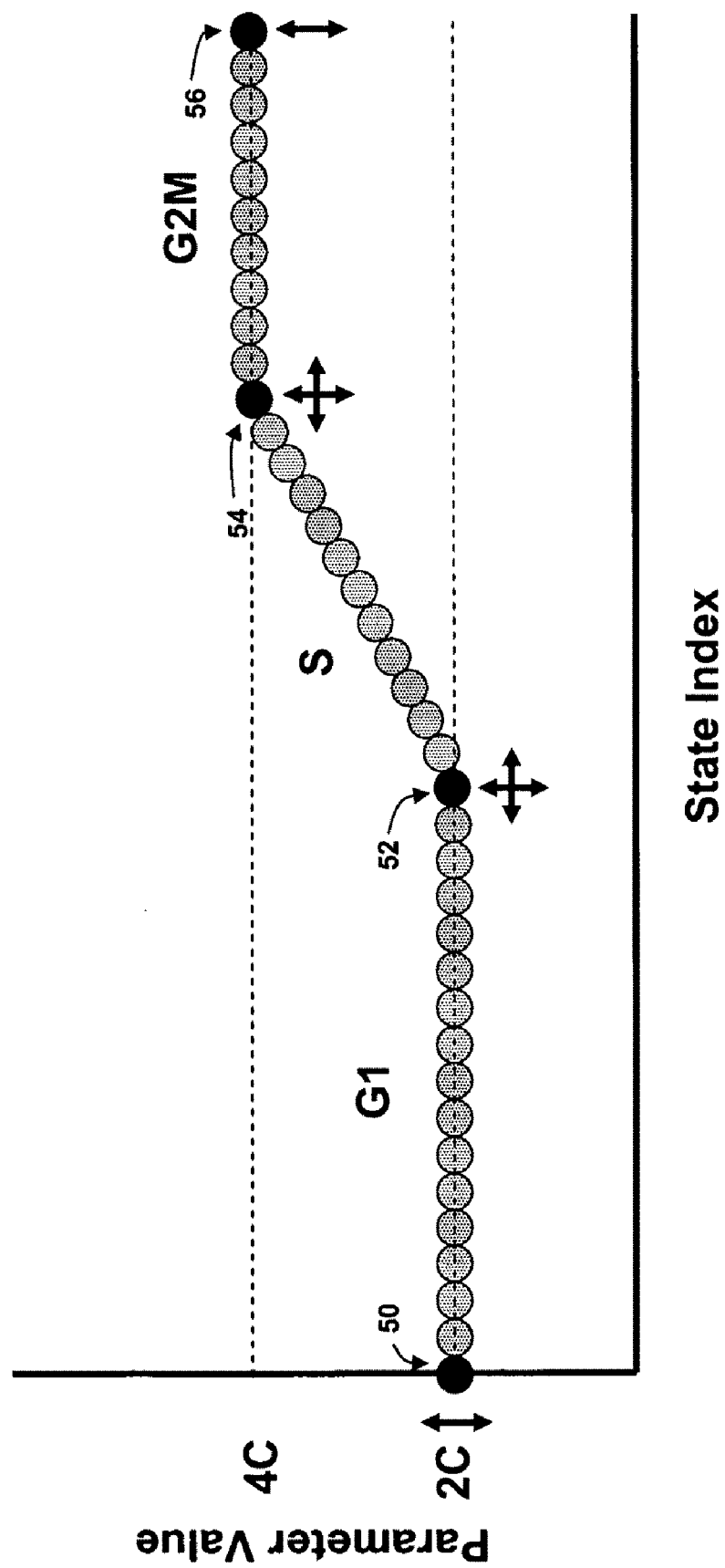
FIG. 6 shows one embodiment of a parameter profile with control definition points.

FIG. 6 illustrates another embodiment of the present invention. The parameter profile illustrated in FIG. 6 is an example of a parameter profile that would be appropriate for the analysis of a cell's DNA content during the course of cellular division. The beginning of the parameter profile, i.e., the portion of the profile between control definition points 50 and 52, represents cells that have 2C amount of DNA and are considered to be in G1 phase of the cell cycle. The middle part of the parameter profile, i.e., the portion of the profile between 52 and 54, is where the cells begin to synthesize DNA (S-phase) to duplicate the genome. The last part of the parameter profile, i.e., the portion of the profile between control definition points 54 and 56, is where cells have 4C amount of DNA (G2M-phase) and are getting ready to divide.

As illustrated in FIG. 6 groups of definition points are controlled by control definition points 50, 52, 54, 56 by some means of interpolation. In one embodiment control definition points can be selected and moved by the user using a standard click and drag techniques. In another embodiment control definition points can be selected by a minimization algorithm. The definition points falling between two control definition points are positioned by interpolation, which in one embodiment may be linear. In other embodiments interpolation may be logarithmic, cubic splines, and/or some other method of interpolation.

Control definition points can have restricted movement or can move in an unrestricted manner. A given control definition point may also have a set of mathematical relations relative to another control definition point, however, mathematical relations between control definition points are not required. Without being bound by any theory, however, it is believed that defining mathematical relations between control definition points increases the stability of a parameter profile when it is modeled. For example, referring to FIG. 6 the state index value of control definition point 52 may be defined as always greater than control definition point 50 and less than control definition points 54 and 56. The parameter value of control definition point 50 may be defined as always equal to control definition point 52 and control definition point 54 always equal to control definition point 56. Alternatively, the control definition point 52 may be restricted to be ½ of control definition point 54's parameter value. In the preferred embodiment of this invention, any number of mathematical relations can be created between any two or more control definition points. Further mathematical relations can be created between control definition points and definition points. The set of definition points, control definition points, and mathematical relations between control definition points is referred to as a parameter profile.

In one embodiment, the positions of one or more control definition points are optimized using a minimization algorithm. Useful minimization algorithms include, but are not limited to, the downhill simplex algorithm and the steepest gradient search algorithm. The response value minimized is the uniformity response value presenting the deviation between an observed frequency distribution and an expected frequency distribution 48. The minimization algorithms optimize the position of the control definition points such that it is equally probable for events to fall into any state index value for a given cell type.

FIG. 7A illustrates one embodiment of optimizing the position of a control definition point. Listmode data are received and a parameter profile is generated as described by control definition points 70a, 70b, 70c, and 70d. In this ideal state, the state index frequency distribution 72 is near uniform 74 with a RCS 76 of 1.01. As illustrated in FIG. 7b, if the control definition point 70b is moved to the left of its ideal position, the state index frequency distribution dramatically changes. Moving from the ideal location creates a distortion in the state index frequency distribution which causes an increase in the uniformity response value 84. Methodically moving this control definition point to the right, left, up, and down forms a uniformity response value surface as indicated in FIG. 7C. The minimization routines can follow the downward gradient of this response surface to find the optimal location of one or more control definition points 70b, 70a, 70c, 70d. Thus, if the optimal control definition points are unknown, they can be estimated by using this minimization method.

As set forth above each definition point has a probability distribution about its parameter value which is used to determine the selection vector for each event. The probability distribution represents the measurement error and intrinsic variability for the value associated with each parameter definition point. For example, linear cytometric parameters generally have measurement errors described by a constant coefficient of variation (cv) and log parameters, by a constant standard deviation (sd). In one embodiment, the probability distributions are estimated using either a cv or sd. In another embodiment, the probability distributions are initially estimated using either a cv or sd and then further refined by the observed sd's.

FIGS. 7A and 7B further depict specific zones defined by the association of certain control definition points with endpoints. Without being bound by any theory, deriving zones from the association of certain control definition points with end-points largely obviates false negative and positive errors caused by conventional data analysis methods that rely upon gating. As illustrated in FIGS. 7A and 7B the end-points are selected to define zones correspond to G1, S, and G2M of the DNA cell cycle. In a preferred embodiment, zones have position, size, and color attributes. Since each event is associated with a single state index and each state index can be associated with a single zone, these zones can be used to color events and single parameter frequency distributions 78b, 80b, 82b. In a preferred embodiment, the last defined zone has priority for these associations. The single parameter frequency distributions 78b, 80b, 82b demonstrate that the zone categories are defined probabilistically where there is appropriate overlap between the G1, S, and G2M categories. A gating approach would not account for the overlapping distributions, creating significant false negative and positive errors. Statistics for each zone can be calculated and displayed as well 78c, 80c, 82c.

Once a state index is selected for an event, the probability of it being the correct selection or its fidelity can be estimated from the underlying selection vector's probability distribution. For the example selection vector {2,4,2,0}, if element 0 were selected, its fidelity would be 0.25. This probability is a complex function of how parameter profiles vary with state index as well as their measurement variability. The state index fidelity for a particular state index is defined as the average of all these probabilities for all events selected for a cell type. State index fidelity plots play an important role in understanding how multiple parameter profiles complement each other when designing multiple parameter state models.

Although the preceding examples have only involved one parameter profile, the state index selection process described above allows any number of parameter profiles to be added to any cell type. These cell type parameter profiles simply stack underneath each other. There can be any number of cell types in a probability state model and the parameter profiles associated with each of these cell types can be different. Before extending the probability state model to incorporate more parameters, there are few important observations to make about the DNA parameter profile illustrated in FIGS. 6 and 7.

The general shape of the DNA Parameter Profile wellestablished and was known before it was added to the probability state model. If there were no a priori information available with regard to this parameter profile, any positional sequence of G1, S and G2M parts of the DNA parameter profile would yield equivalent results (data not shown). Accordingly, in a preferred embodiment when modeling multiple probability state models the parameters that have the most a priori information about their state distribution are modeled first.

Figures 8A, 8B, 8C, 8D, 8E:
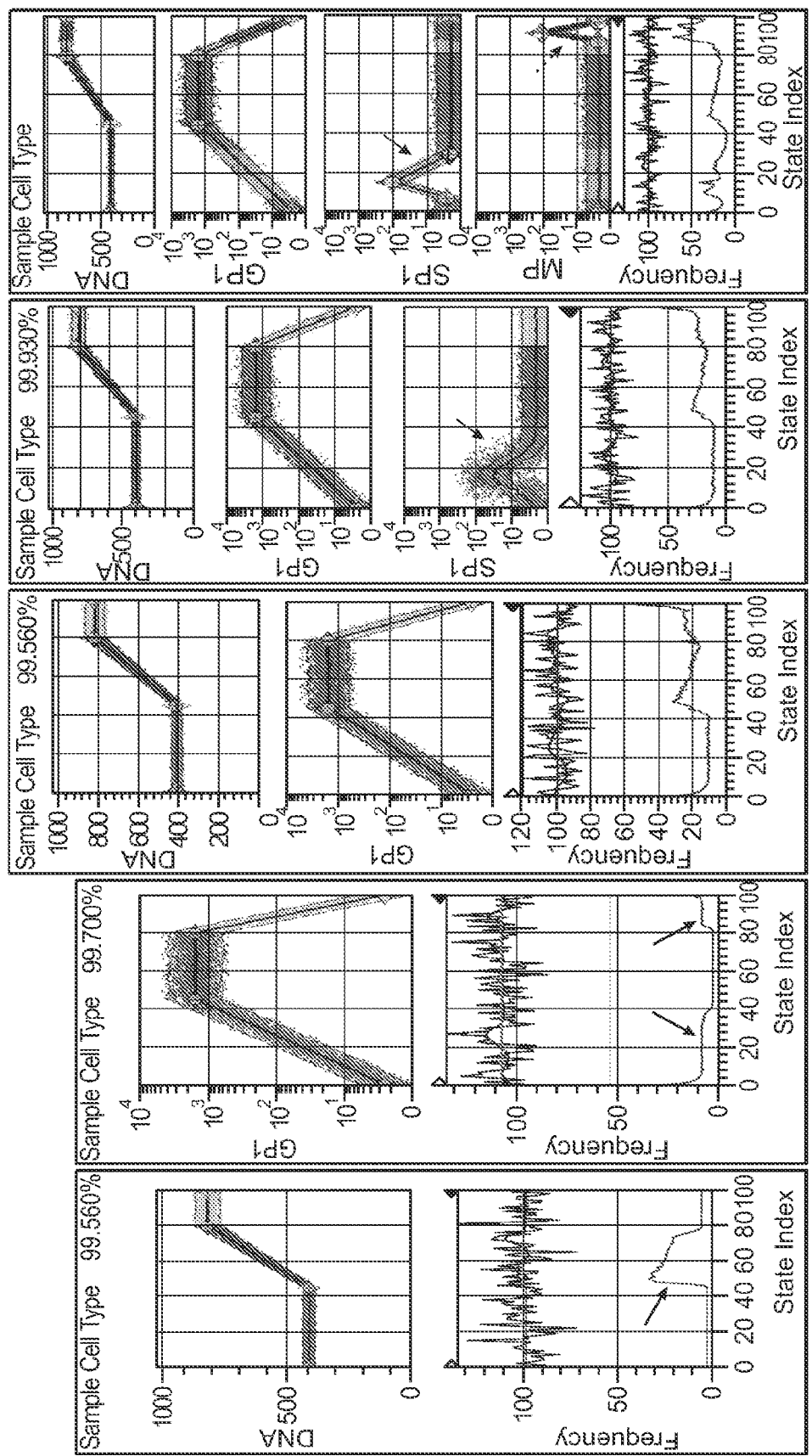
FIG. 8 depicts one embodiment of the process of building a multiple parameter probability state model.

Referring to FIGS. 8A through 8E, it is observed from the state index fidelity plot that the S-Phase portion of the DNA parameter profile conveys most of the information that associates a state index to a DNA parameter value. In FIG. 8A, the G1 and G2M zones have relatively lower state index fidelity values because their intensities do not vary with state index. The fidelity plot's downward slope in S-Phase, as indicated by the black arrow, is attributable to the increasing measurement uncertainty associated with higher S-phase parameter values. The colors of the data points are determined by G1 (red), S (blue), and G2M (green) Zones.

Contrast the DNA parameter profile's fidelity plot with the fidelity plot for a second parameter profile derived from synthesized data labeled as "GP1". See the black arrows on FIG. 8B). This state index fidelity plot is higher in the G1 zone, lower in the S-Phase zone, and higher again in the G2M zone. The GP1 parameter profile also simulates log parameter data where the measurement variability is relatively constant and therefore independent of the parameter intensity. Examination of its state index fidelity plot reveals that this parameter is complementary to the DNA parameter profile, where fidelity values that are low in one fidelity plot are relatively high in the other.

When complementary parameter profiles like those shown in FIGS. 8A and 8B are combined in a probability state model, the resultant state index fidelity plot shows that all state index regions now have reasonably high fidelity values. (See FIG. 8C.) Probability state models with complementary parameter profiles are referred to as "well-defined" and have some very important characteristics.

If another parameter, SP1, is added to this model, its distribution as a function of state index is now determined by the preceding two parameter profiles without the need for creating a new parameter profile. (See FIG. 8D.) This means that once a probability state model is well-defined by complementary parameter profiles, completely unknown parameters can be investigated by simple inspection. As shown in FIG. 8D, SP1 is up-regulated in early G1. Given this observed distribution, an appropriate parameter profile for SP1 can be added and fitted to the data, making the model even better defined for other measured parameters. (See FIG. 8E.) A corresponding zone (light blue) was added to uniquely color events in the SP1 up-regulated area.

In this four-color simulation, a fourth parameter labeled "MP" is shown to be up-regulated in the G2M phase. (See FIG. 8E) An additional zone was created for this subpopulation (dark green). An important characteristic of this invention is that the stacked graphics shown in FIG. 8E succinctly summarize all of the important parameter correlations in the model.

Frequently it is important to visualize a probability state model's parameter profiles with conventional two parameter and three parameter displays. Since each event is eventually associated with a specific cell type zone, coloring the data points with matching zone colors is a natural way of viewing conventional displays.

Figure 9:
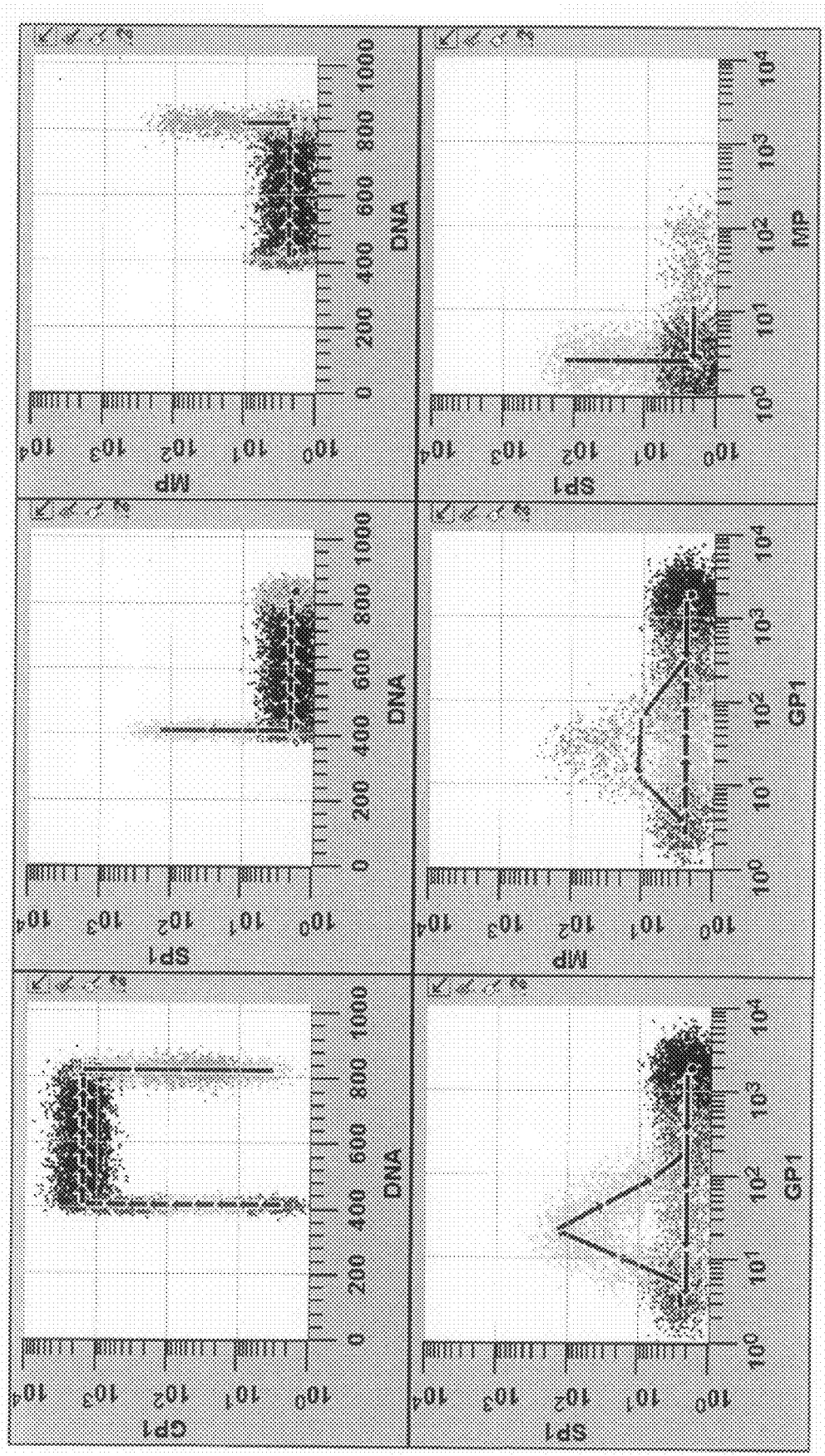
FIG. 9 depicts one embodiment of plots of multiparameter data plotted using zone colors and state vectors.

Another graphical technique that is possible with this invention is to segment the state index axis into some programmable number of vectors (e.g. 20). To view these vectors in a 2P display, the system associates the end points of the state vectors with corresponding parameter profile definition points or parameter mean values. FIG. 9 displays all combinations of the four parameters shown in FIG. 8 using these techniques. The DNA vs. GP1 two-parameter display is relatively easy to interpret. The data begins in the lower-left portion of the display and "flows" up to the beginning of S-Phase, then across S-Phase to the beginning of G2M, and then down to the end of G2M. Other parameter combinations, such as the SP1 vs. G1P and SP1 vs. MP, are more difficult to interpret. The "flow" of the data can double back on itself and can create complex loops. Prior art methods of displaying one measured parameter versus another may not always be the best way of interpreting correlations.

Multiple Sample Integration

For many reasons, most laboratories will analyze a specimen with a set of reagent panels. Each panel is used to create a sample listmode file that examines the specimen in a different way. Typically, samples have between five and seven measured parameters, but this number is continually increasing with newer instrumentation and reagents. The general idea is to use all the samples to obtain a coherent picture of what is happening in the specimen. In many cases, the number of one parameter and two parameter graphs to convey this information can be in the hundreds.

Figure 10:
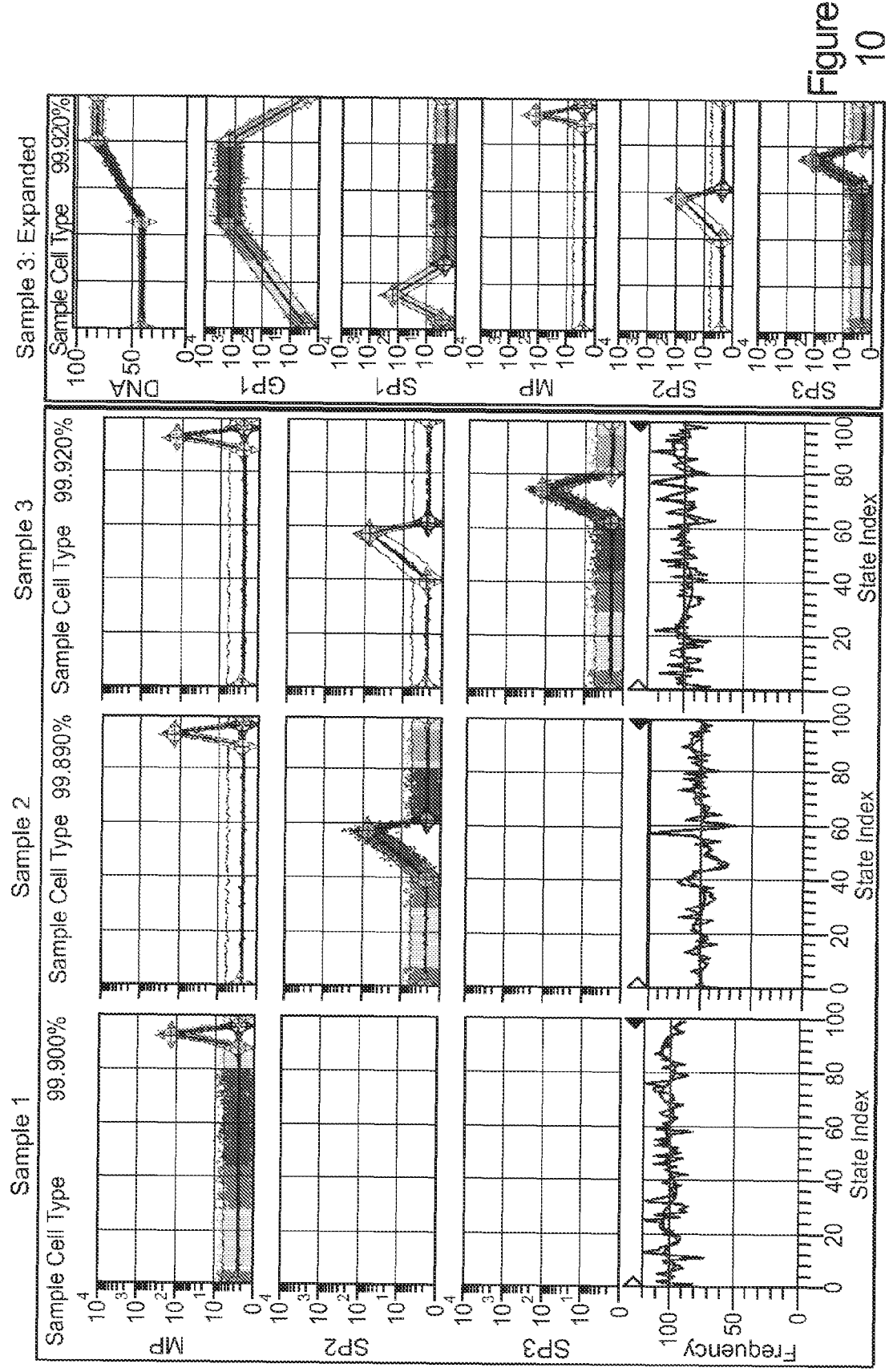
FIG. 10 depicts a single probability state model representing multiple related samples in accordance with one embodiment of the present invention.

When a probability state model has a well-defined set of complementary parameter profiles, the model can potentially span multiple samples. FIG. 10 shows how this works for three simulated listmode files labeled "Sample 1", "Sample 2", and "Sample 3". Sample 1 contains the parameters DNA, SP1, GP1, and MP; Sample 2, DNA, SP1, GP1, and SP2; and Sample 3, DNA, SP1, GP1, and SP3. Sample 1 is the same data and model shown in FIG. 8, Panel E with just the MP parameter profile showing. The other parameter profiles have been collapsed to better optimize the viewing area. Parameter profiles SP2 and SP3 have been added to the model, but since they don't match any of Sample 1's parameters, no data appears.

When Sample 2 is read into the model, the event data points disappear from the MP parameter profile, but the means, definition points, and measured confidence limits remain. These statistics provide a data envelop that represents the data as it was defined in the first sample. The SP2 parameter profile is now "live" and can be fit with the appropriate parameter profile as shown in FIG. 10, Sample 2. When Sample 3 is read into the model, both the MP and SP2 statistical data envelops remain, and the SP3 Parameter Profile is now "live". After all the samples have been added, the model can be expanded and all the relevant parameter profiles from the three separate samples can be reviewed together. Immediately evident from this plot is that SP1 is up-regulated in early S-Phase whereas, SP2 is up-regulated in late S-Phase. If one or more of the common parameters in these listmode files change during the analysis, the model shows a distorted state index frequency with a relatively high RCS value (data not shown) alerting the user to the change. Since a probability state model is a probability-based system, a p-value can be used to verify that the common parameters have not changed significantly during the analyses (data not shown). Even if there are not a strong set of complementary common parameter profiles in the samples, a single model can span multiple samples. A good example of this will be described later in the B Lymphoid Maturation example.

Analysis of Multiple Cell Types

Figure 11:
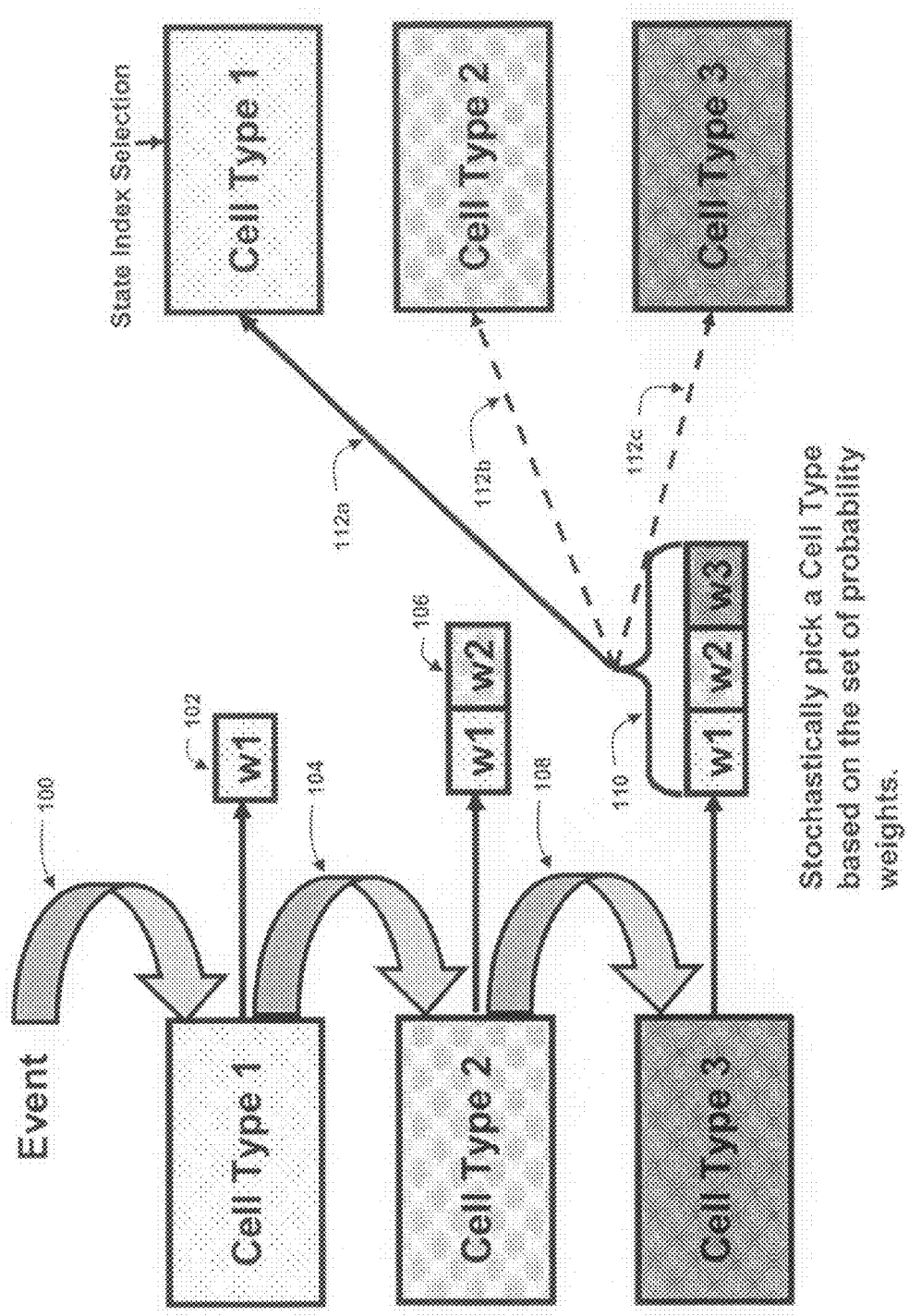
FIG. 11 depicts the process of cell type selection according to one embodiment of the present invention.

In other aspects the present invention provides for the analysis of multiple cell types. FIG. 11 illustrates one embodiment of the present invention for analysis and display of multidimensional data obtained from multiple cell types. As illustrated in FIG. 11 an event 100 is processed by the first cell type defined in the system. The summation of the selection vector is used to form cell type weight 102. This cell type weight is normalized by a cell type bias so that it is comparable to the other defined cell types.

Next, the event is processed by the next cell type 104 and a weight for this cell type is calculated and added to a weight vector 106. This process continues for all the defined cell types 108, creating a single vector of weights 110. This weight vector is then used to stochastically choose a cell type 112a, 112b, 112c. Once a cell type has been chosen 112a, a state index is selected as described earlier. (See FIGS. 4 and 5.)

Figure 12:
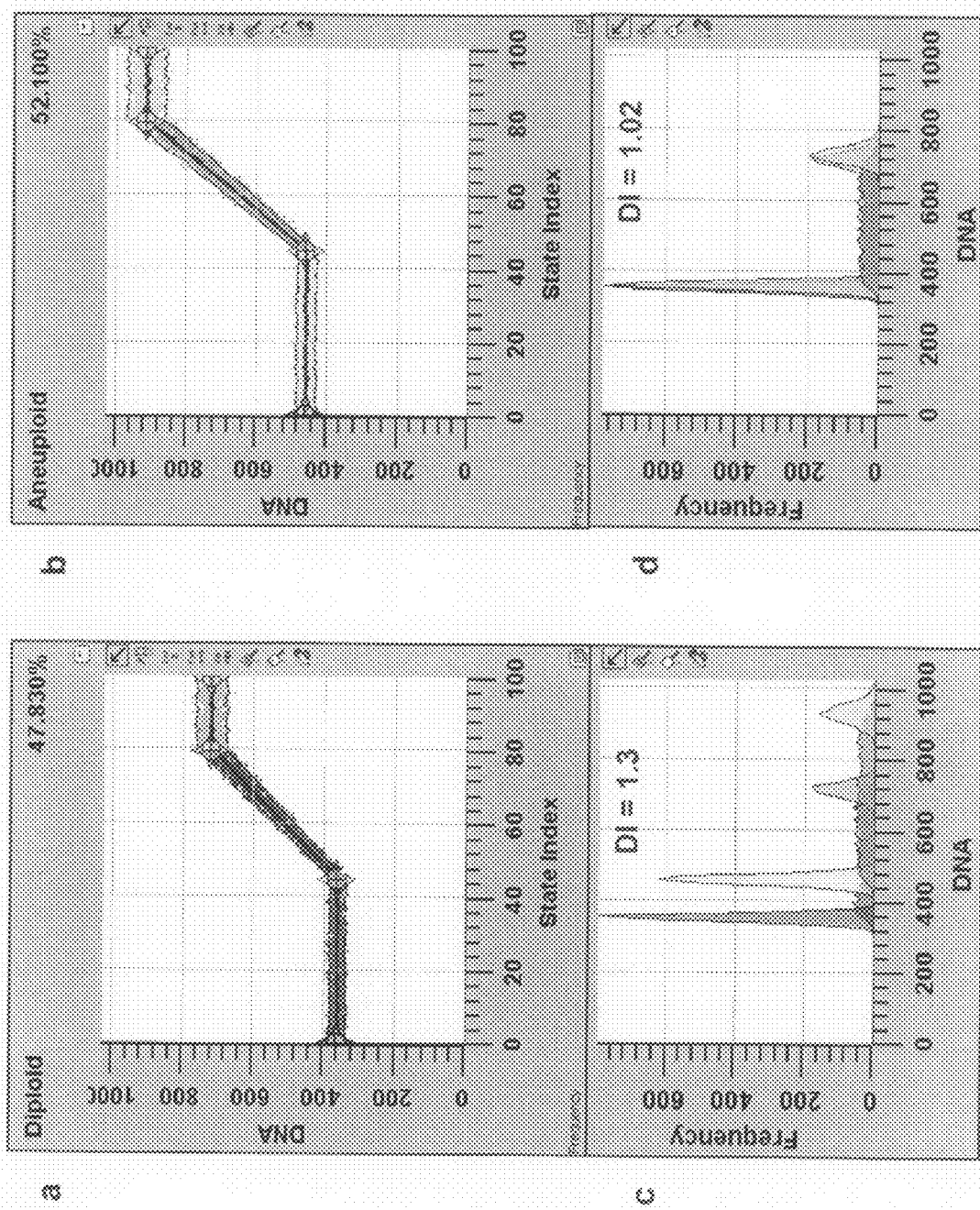
FIG. 12 depicts one embodiment of a two cell type probability state model for a DNA Diploid and Aneuploid.

FIG. 12a illustrates a DNA diploid cell type and FIG. 12b shows a DNA aneuploid cell type using the cell type selection process set forth herein. A DNA diploid population has a normal amount of DNA during its cell cycle; whereas, a DNA aneuploid population has an abnormal amount of DNA. FIGS. 12c and 12d illustrate the DNA diploid and aneuploid histograms for DNA Index (DI), the ratio of the DNA aneuploid G1 to the DNA diploid G1, of 1.3 and 1.02 respectively. FIGS. 12c and 12d demonstrate that the analysis method of the present invention is capable of accounting for the overlapping distributions for the G1, S, and G2M cell cycle phases for both the DNA diploid and aneuploid populations.

Analysis of Multiple State Models for a Cell Type

In other aspects the present invention relates to a method for analyzing multiple state models for a single cell type. A state model may be defined as set of progressive states involved in a cell dividing as shown in FIGS. 6 and 7. A state model may also define the processes associated with cell signal transduction. Accordingly, cells may have multiple state models that are either independent or in some way related.

Figure 13:
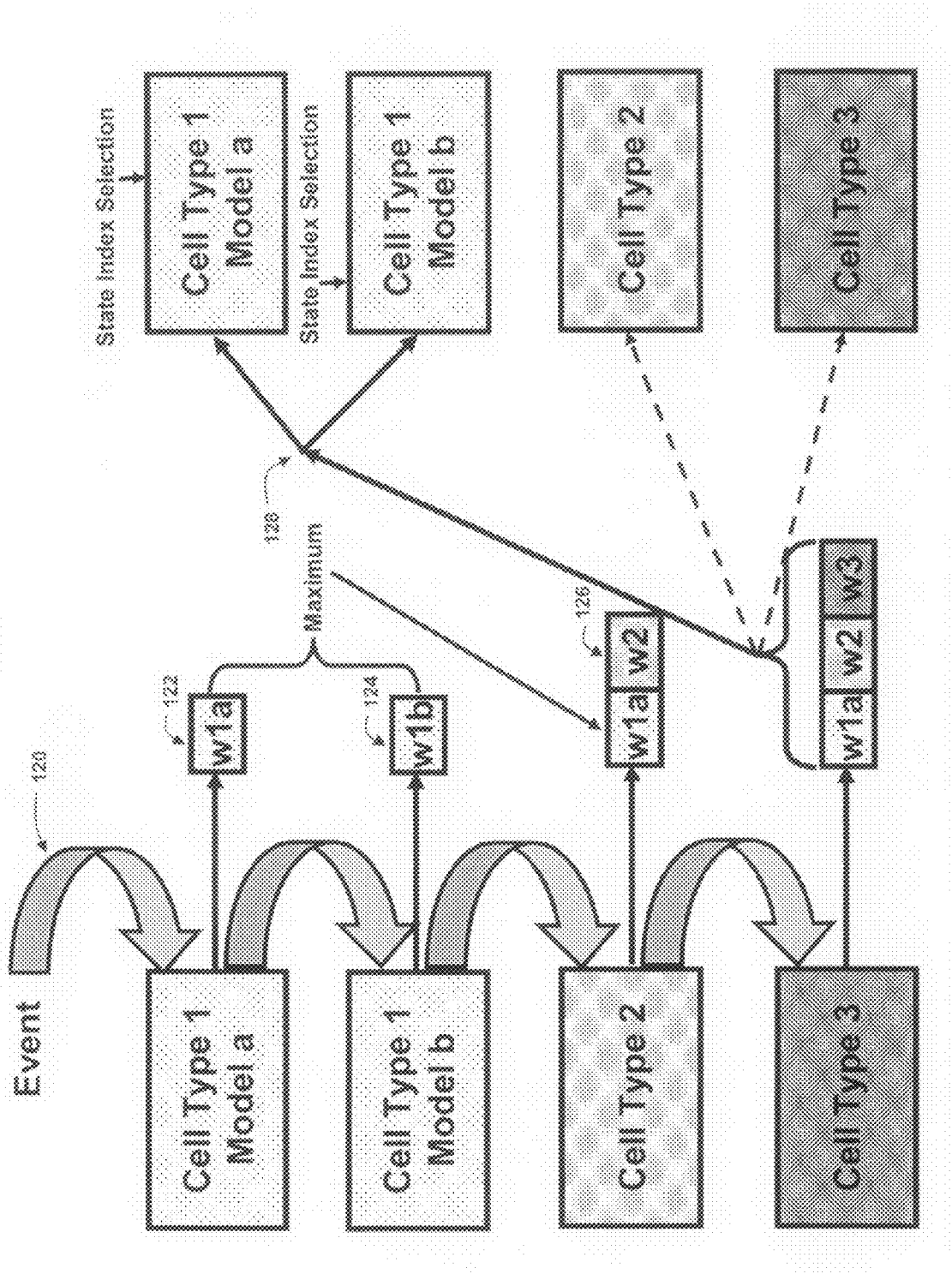
FIG. 13 depicts one embodiment of the process of cell type selection for multiple probability state models.

FIG. 13 illustrates one embodiment of analyzing parameters that may be part of different state models for a single cell type. The method of analyzing multiple state models for a single cell type comprises defining cell type 1 as having two different parameter profiles relating to two different state models, State Model A and State Model B. A cell type weight w1A 122 is generated for Cell Type 1, State Model A and a cell type weight w1B 124 is generated for State Model B. The maximum of these two weights 122, 124 is then selected and the value is added to the weight vector 126. A cell type is then determined as described above with regard to FIG. 11. In the event that the selected cell type is one that has multiple state model variants 128, the state index selection is performed on each variant.

Programs and Systems for Performing Probability State Model Fitting

Figure 15:
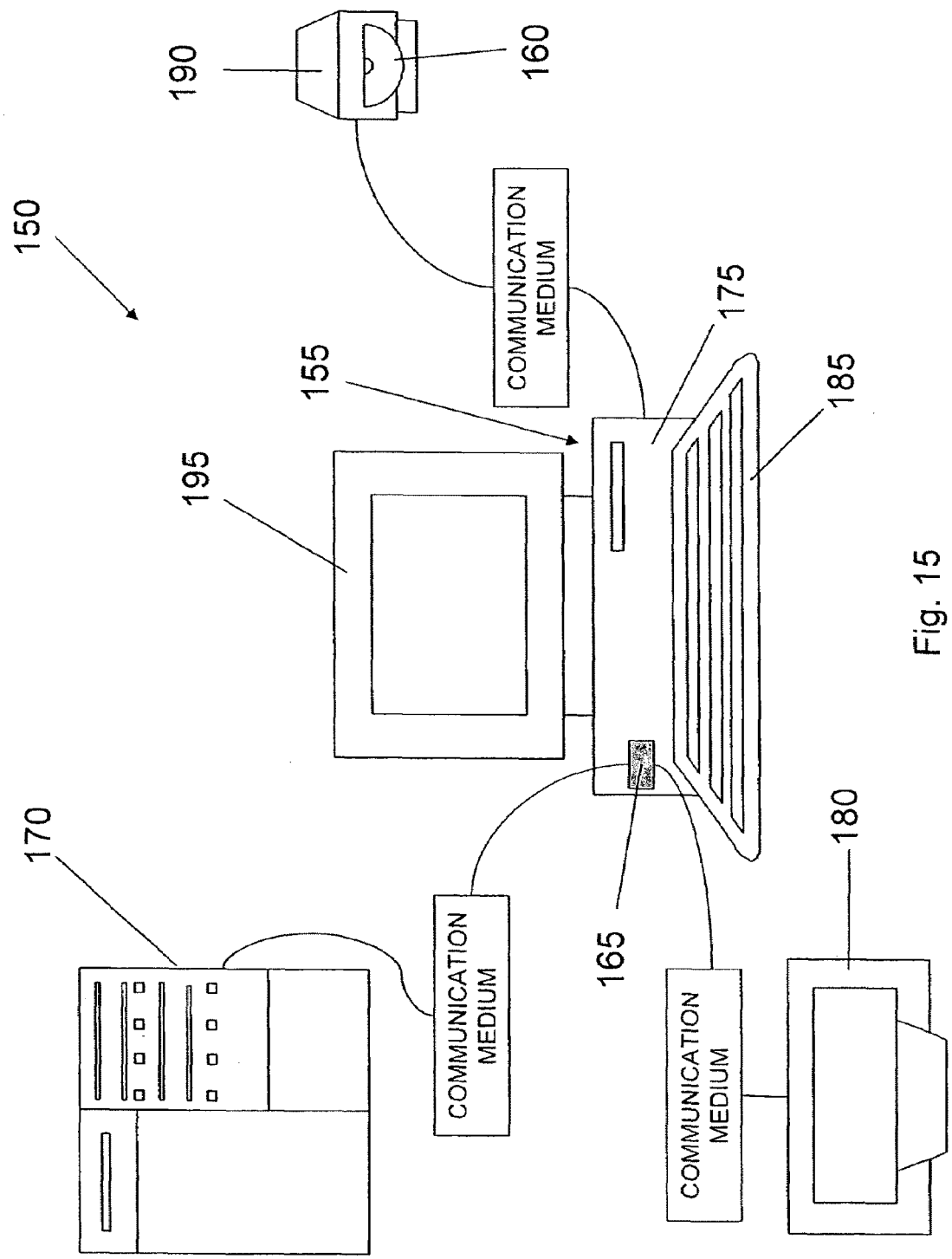
FIG. 15 depicts a block diagram of a system in which various aspects of the invention may be embodied.

FIG. 15 is a block diagram illustrating a system which various aspects of the present invention may be embodied. As will be understood by those skilled in the art the present invention can be implemented in hardware and/or software. In certain embodiments different aspects of the invention can be implemented in either client-side logic or server-side logic. As further understood by those skilled in the art a computing device, such as a personal computer, may be configured to receive a fixed media program component containing logic instructions and/or data that when loaded into the computing device cause that device to perform according to the invention. In certain embodiments the fixed media containing logic instructions may be delivered to the user on a fixed media for physically loading into the computing device or the computing device may accesses a remote server through a communication medium in order to download a program component containing the logic instructions.

FIG. 15 illustrates one embodiment of a system 150 according to the present invention. In the present embodiment the system comprises a personal computer 155 that can read instructions from fixed media 160 and/or network port 165, which can optionally be connected to server 170. The personal computer 155 of the present embodiment contains a CPU 175, and optionally one or more input devices, such as a keyboard 185, or a mouse, a disk drive 190 or a monitor 195. The personal computer may be programmed by accessing instructions stored on the fixed media 160, or the server 170. In specific embodiments, the invention may be embodied in whole or in part as software recorded on the fixed media 160 or the server 170.

Optionally, the personal computer 155 is in communication with or integrated with a flow cytometer system 180.

The invention also may be embodied in whole or in part within the circuitry of an application specific integrated circuit (ASIC) or a programmable logic device (PLD). In such a case, the invention may be embodied in a computer understandable descriptor language, which may be used to create an ASIC, or PLD that operates as herein described.

The present invention further embodies integrated systems for carrying out data analysis. In one embodiment the present invention provides an integrated system for analyzing cytometry data, as well as for the compilation, storage and access of databases. Typically an integrated system comprises a digital computer with software including an instruction set as described herein.

Readily available computational hardware resources using standard operating systems can be employed and modified according to the teachings provided herein, e.g., a personal computer for use in the integrated systems of the invention. Current art in software technology is adequate to allow implementation of the methods taught herein on a computer system. Thus, in specific embodiments, the present invention can comprise a set of logic instructions (either software, or hardware encoded instructions) for performing one or more of the methods as taught herein. For example, software for providing the described data and/or statistical analysis can be constructed by one of skill using a standard programming language such as Visual Basic, Fortran, Basic, Java, or the like. Such software can also be constructed utilizing a variety of statistical programming languages, toolkits, or libraries.

Various programming methods and algorithms can be used to perform aspects of the data collection, correlation, and storage functions, as well as other desirable functions, as described herein. In addition, digital or analog systems such as digital or analog computer systems can control a variety of other functions such as the display and/or control of input and output files. Software for performing the statistical methods of the invention, such as programmed embodiments of the statistical methods described above, are also included in the computer systems of the invention. Alternatively, programming elements for performing such methods as least squares analysis can also be included in the digital system to identify relationships between data. Optionally, the integrated systems of the invention include an automated workstation.

The system of the present invention may also include a variety of commercially available peripheral equipment for acquisition of multidimensional data. For example, commercially available peripheral equipment may include a flow cytometry system, a spectral imaging system, a microarray imaging system, an optical system used to measure parameters, one or more sensors or detector used to measure parameters, or any other data acquisition devices known in the art for providing one or more parameters for a plurality of events. One skilled in the art will recognize that numerous available systems are capable of generating multidimensional data that may be analyzed according to the present invention and further that the present invention is not limited to any particular type of multidimensional data sets or acquisition systems.

Figure 16:
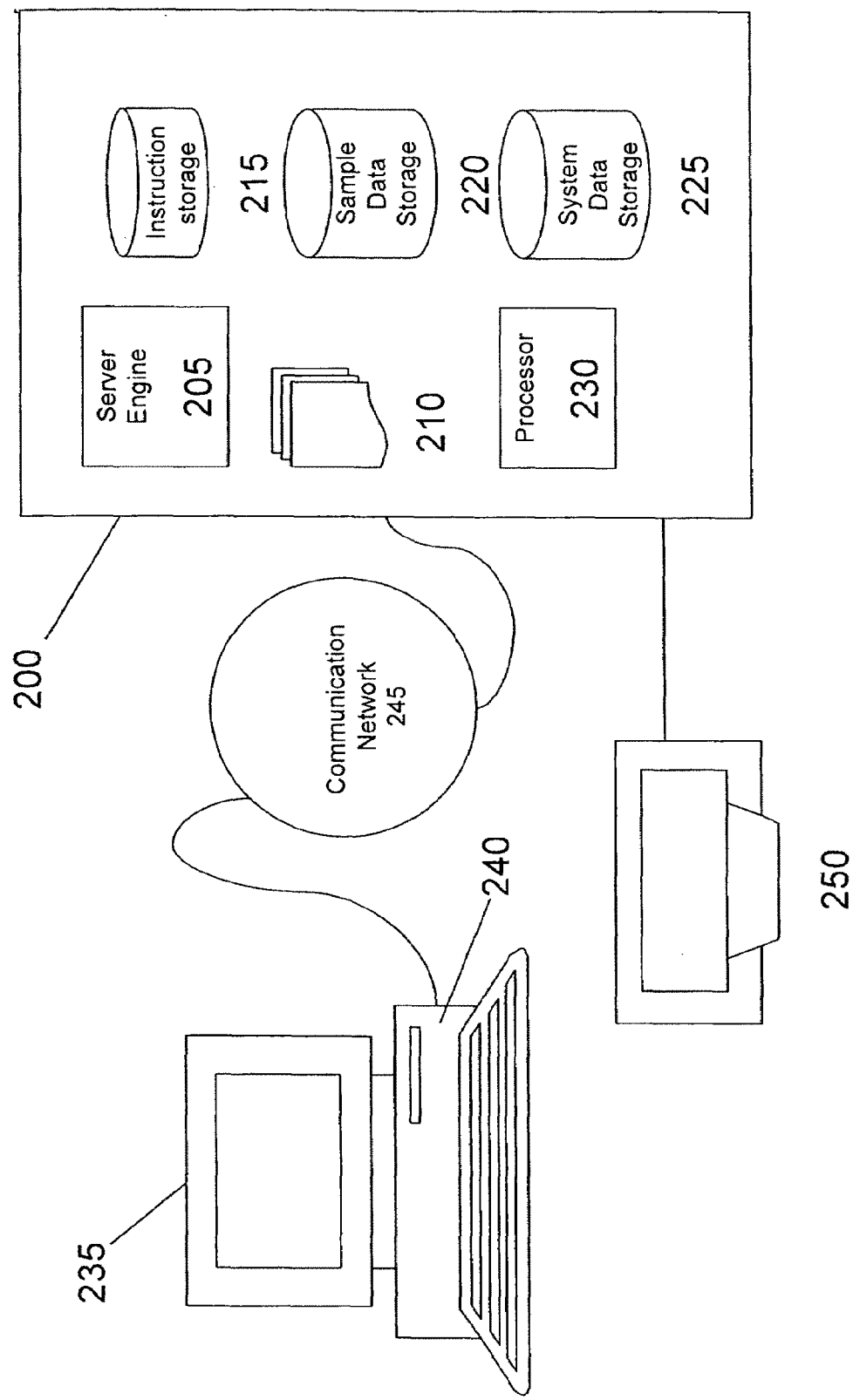
FIG. 16 depicts a block diagram of an alternative system in which various aspects of the invention may be embodied.

FIG. 16 is a block diagram illustrating a system according to another embodiment of the present invention. The embodiment illustrated in FIG. 16 enables data analysis according to the methods of the present invention operating over a network. The server system 200 includes a server engine 205, various interface pages 210, data storage 215 for storing instructions, data storage 220 for storing sample data, and data storage 225 for storing data generated by the system. According to specific embodiments of the invention, the server system further includes or is in communication with a processor 230 that further comprises one or more logic modules for performing one or more methods as described herein.

Optionally, one or more client systems may also comprise any combination of hardware and/or software that can interact with the server system. These systems may include a personal computer or workstation 235 including a logic interface module, such as a web browser 240 and/or various other systems or products through which data and requests can be communicated to a server system, which are in communication with the server system 200 via a communication network 245.

Optionally, the server system 200 is in communication with or integrated with a flow cytometer system 250.

EXAMPLES

The following examples of analyzing and displaying multidimensional data are now disclosed. The following examples are illustrative in nature of various aspects of the present invention and are not intended to be limiting in any manner.

Analysis and Display of DNA Content and Cell Volume

Raw data generated by a NPE cytometer measuring tumor cells stained with Propidium Iodide (PI), a DNA specific dye, were received by the computer. The cytometer produces a two-parameter listmode file comprising DNA and cell volume parameters. In FIG. 14A the analysis reveals that for the DNA Aneuploid population, cell volume starts to increase in late G1 well before the commencement of S-Phase.

Analysis and Display of B Lymphoid Maturation in Normal Bone Marrow

FIG. 14B shows the results of an analysis of two samples of a normal bone marrow specimen. The parameters in the first sample analyzed were FALS, SS, CD22 (FITC), CD34

(PE), CD19 (APC) and CD45 (PerCP) and in the second were FALS, SS, CD20 (FITC), CD10 (PE), CD19 (APC), and CD45 (PerCP). The parameter profiles (not shown) were chosen based on published data (2) and only the means and confidence limits are shown to simplify the display. This specimen's changes in B lymphoid states as a function of maturation are shown for Stages I, II, III, and IV. The CD19 intensity remains relatively invariant until Stage IV, where it drops slightly. The SS slowly increases as the B-cell matures. CD34 drops quickly in the maturation process and remains low. CD22 is slightly high early on, then drops to negative intensity and then increases again in the final stages of maturation. CD20 is initially negative and then begins to slowly increase during maturation, eventually leveling off. CD10 is initially high and then quickly drops near the end of the B-cell's maturation. It is worth noting that the prior art methods of analyzing this data would normally involve reports with well over 10 2P plots.

The CD20 vs. CD10 contextual plot show colored data points representing some of the B-cell maturation stages as well as a state vector plot, giving the data directionality. Finally, the SSC vs. CD45 plot shows the classic increase in CD45 as a function of lymphoid maturation (2, 3). The light gray data points are the waste events that were not categorized by the invention.

The number of states for all the examples shown herein was 100. This was an entirely arbitrary decision and could have been 20 or 200 without significantly affecting any of the analyses. With more states there are more calculations necessary to create the selection vector. With 100 states, the minimization algorithm for the DNA examples took about 10 to 15 seconds of processing time on a typical personal computer. As the complexity of a probability state model increases, it may be advantageous to reduce the number of states. In the event that probability state model were to be used to provide real-time sorting decisions, there would be impetus to minimize the number of states. If parameters have a lot of complexity and relatively low measurement error, then it may be of benefit to increase the number of states.

What is claimed is:

1. A system for generating a probability state model, the system comprising:
   a detector; and
   a computer operably connected to the detector, wherein the computer accesses one or more logic instructions for receiving raw data at the computer and generating a probability state model display of one or more parameters associated with the raw data, wherein the probability state model comprises one or more parameter profiles comprising a plurality of distribution points, and wherein each distribution point is mapped to a parameter, an event, an a state index, wherein the computer performs the steps of:
   a. storing one or more retrievable models in a memory portion in communication with the computer, wherein:
      i. each of the one or more retrievable models comprises at least two control definition points and two intermediate definition points associated with a measurable parameter and plotted against state index values comprising a progression index, and
      ii. each definition point further comprises a probability distribution curve;
   b. receiving raw data for at least one parameter, wherein the raw data comprises a plurality of observed event measurements for the at least one parameter;
   c. applying each of the plurality of observed event measurements to one of the one or more retrievable models;
   d. calculating a probability weight for each state based on the probability that each of the plurality of observed event measurements coincides with the probability distribution curve for each of the one or more control definition points and/or intermediate definition points;
   e. creating a state selection vector for each of the plurality of observed event measurements based on the calculated probability weights for the progression of state index values;
   f. stochastically selecting a specific state index value from the state selection vector calculated in step d) based on the probability weights wherein the specific state index value selected determines the definition point associated with that state index value for each of the one or more parameters;
   g. incrementing a frequency counter representing the frequency that each of the control definition points and intermediate definition points are stochastically selected in step f) for each state index in the progression;
   h. displaying a parameter profile on a graphical user interface at a display terminal in communication with the computer, wherein the parameter profile comprises definition points for one or more events that are plotted against the progression of state index values, such that each state index value in a full progression of state index values is associated with a definition point;
   i. analyzing the frequencies of the control definition points and intermediate definition points throughout the progression for uniformity;
   j. moving the control definition points left and right and the intermediate definition points left, right up, and down along the parameter profile to produce uniform frequencies across the progression; and
   k. displaying said parameter profile on said graphical user interface in communication with the computer, wherein the plurality of observed event measurements for each of the one or more parameters are a function of state index.

2. The system of claim 1 wherein the one or more logic instructions accessed by the computer are stored on a fixed media.

3. The system of claim 1 further comprising a remote server and a communication network, wherein the one or more logic instructions are stored on the remote server, which is accessed by the computer via the communication network.

4. The system of claim 1 further comprising one or more input devices.

5. The system of claim 1 further comprising a display.

6. The system of claim 1 wherein the detector is a cytometer.

7. A method of analyzing multidimensional data using a computer comprising the steps of:
   a. storing one or more retrievable models in a memory portion in communication with the computer, wherein:
      i. each of the one or more retrievable models comprises at least two control definition points and two intermediate definition points associated with a measurable parameter and plotted against state index values comprising a progression index, and
      ii. each definition point further comprises a probability distribution curve;
   b. receiving raw data for at least one parameter, wherein the raw data comprises a plurality of observed event measurements for the at least one parameter;
   c. applying each of the plurality of observed event measurements to one of the one or more retrievable models;
   d. calculating a probability weight for each state based on the probability that each of the plurality of observed event measurements coincides with the probability distribution curve for each of the one or more control definition points and/or intermediate definition points;

e. creating a state selection vector for each of the plurality of observed event measurements based on the calculated probability weights for the progression of state index values;

f. stochastically selecting a specific state index value from the state selection vector calculated in step d) based on the probability weights wherein the specific state index value selected determines the definition point associated with that state index value for each of the one or more parameters;

g. incrementing a frequency counter representing the frequency that each of the control definition points and intermediate definition points are stochastically selected in step f) for each state index in the progression;

h. displaying a parameter profile on a graphical user interface at a display terminal in communication with the computer, wherein the parameter profile comprises definition points for one or more events that are plotted against the progression of state index values, such that each state index value in a full progression of state index values is associated with a definition point;

i. analyzing the frequencies of the control definition points and intermediate definition points throughout the progression for uniformity; and j. moving the control definition points left and right and the intermediate definition points left, right up, and down along the parameter profile to produce uniform frequencies across the progression; and k. displaying said parameter profile on said graphical user interface in communication with the computer, wherein the plurality of observed event measurements for each of the one or more parameters are a function of state index.

8. The method of claim 7, further comprising identifying control definition points wherein mathematical relations exist between the control definition points and between the control definition points and plurality of definition points.

9. The method of claim 7 further comprising calculating a running mean and standard deviation of frequency.

10. The method of claim 9 further comprising associating a frequency, mean and standard deviation to each state index value in the progression after all of the plurality of observed event measurements are applied to the one or more retrievable models.

11. The method of claim 10 further comprising displaying bands around the observed event measurements in the displayed parameter profile, wherein the width of each band is a fraction of the standard deviation and the center of each band is the mean observed event measurement value for each state.

12. The method of claim 7 further comprising a step after j) of repeating steps f) through j) until the frequencies are uniform throughout the progression.

13. The method of claim 7 wherein the probability weights calculated in step d) are a function of each of the plurality of observed event measurements intersecting one or more probability distribution curves associated with the control definition points and/or intermediate definition points.

14. The method of claim 13, wherein the raw data comprises observed event measurements for two or more parameters and the probability weights are determined by multiplying the probability weights of both definition points at each state index value in the progression.

15. The method of claim 13 wherein the probability weights are determined by Chi Square analysis.

16. The method of claim 7, wherein the parameter profile comprises a model displaying the two or more parameters correlated with one another as a function of state index values.

17. The method of claim 7, further comprising interpolating definition points between the control definition points and intermediate definition points.

18. The method of claim 7 further comprising the step of defining at least one zone on the parameter profile wherein a zone is defined as definition points bounded by control definition points and/or intermediate definition points.

19. The method of claim 7 further comprising the step of assigning to the zone an attribute selected from the group consisting of position, size and color.

20. The method of claim 7 wherein each progression of state index values represents a type of event.

21. The method of claim 20 wherein a type of event is a cell type and the plurality of observed event measurements are measured by a cytometer.

* * * * *